(12) United States Patent
Bera et al.

(10) Patent No.: US 8,530,397 B2
(45) Date of Patent: Sep. 10, 2013

(54) ADDITIVE COMPOSITIONS

(75) Inventors: Tushar Kanti Bera, Franklin Park, NJ (US); Rolfe J. Hartley, Rockaway, NJ (US); Jacob Emert, Brooklyn, NY (US); Jie Cheng, Edison, NJ (US); Theodore E. Nalesnik, Hopewell Junction, NY (US); Robert G. Rowland, Woodbridge, CT (US)

(73) Assignees: Infineum International Limited (GB); Chemtura Corporation, Middlebury, CT (US)

( * ) Notice: Subject to any disclaimer, the term of this patent is extended or adjusted under 35 U.S.C. 154(b) by 310 days.

(21) Appl. No.: 11/954,249

(22) Filed: Dec. 12, 2007

(65) Prior Publication Data

US 2009/0156448 A1    Jun. 18, 2009

(51) Int. Cl.
*C10M 133/00* (2006.01)

(52) U.S. Cl.
USPC .............. 508/545; 508/500; 508/556; 44/432

(58) Field of Classification Search
USPC .................. 508/500, 557, 545, 556, 558, 559, 508/563; 44/426, 427, 432; 252/401
See application file for complete search history.

(56) References Cited

U.S. PATENT DOCUMENTS

| | | | | |
|---|---|---|---|---|
| 3,761,405 | A | * | 9/1973 | Jervis et al. .................... 508/477 |
| 5,207,939 | A | | 5/1993 | Farng et al. .............. 252/51.5 R |
| 5,213,699 | A | | 5/1993 | Babiarz et al. .................. 252/50 |
| 5,232,614 | A | | 8/1993 | Colclough et al. ........ 252/32.7 E |
| 5,298,662 | A | | 3/1994 | Smith et al. .................... 564/434 |
| 2006/0052260 | A1 | | 3/2006 | Duyck et al. .................. 508/527 |
| 2007/0006855 | A1 | | 1/2007 | Malandro et al. ........ 123/568.12 |
| 2007/0123438 | A1 | * | 5/2007 | Ma ................................ 508/195 |

* cited by examiner

*Primary Examiner* — Taiwo Oladapo

(57) ABSTRACT

Compositions in the form of lubricating oil compositions, greases, fuels or functional fluids containing, in the form of Michael adducts, N-substituted phenylenediamine additives in which at least one of the substituents on the N atoms carries a carbonyl group that is connected to an alkyl, alkoxyalkyl, or alkylthioalkyl group either directly or via an oxygen atom.

20 Claims, No Drawings

ADDITIVE COMPOSITIONS

FIELD OF THE INVENTION

The present invention relates to compositions in the form of lubricating oil compositions, greases, fuels or functional fluids subject to oxidative degradation, containing, in the form of Michael adducts, substituted phenylenediamine additives.

BACKGROUND OF THE INVENTION

Lubricants (also referred to as lubricant compositions, lubricating oils or lubricating oil compositions), such as those used in a variety of machinery, are susceptible to oxidative deterioration during storage, transportation and usage, particularly when such lubricants are exposed to high temperatures and iron catalytic environments, which greatly promote their oxidation. This oxidation, if not controlled, contributes to the formation of corrosive acidic products, sludge, varnishes, resins and other oil-insoluble products, and may lead to a loss of designated physical and tribological properties of the lubricants. These oxidation products may lead to the formation of harmful deposits on critical engine parts, such as the pistons, piston liners, valves and valve lifters. It is therefore a common practice to include deposit-control and anti-oxidant additives in lubricants to prevent, at least to some extent, oxidation so as to extend their useful life.

Lubricants containing various secondary diarylamines as antioxidants are known in the art. The use of para-phenylene-diamines is also known. Para-phenylene-diamines have more commonly been employed as motor fuel stabilizers and antiozonants and antioxidants for rubber.

U.S. Pat. No. 5,232,614 describes substituted para-phenylenediamines as effective antioxidants capable of protecting crankcase lubricating oils from thickening and sludge formation after prolonged exposure to oxygen at elevated temperature.

US-A-2006/0052260 describes para-phenylenediamine hydrazide compounds as antioxidants, particularly in lubricating oil compositions, including, in Example 1, the production of a Michael adduct of a phenylenediamine and butyl acrylate as an intermediate to make such a hydrazide.

US-A-2007/0006855 describes addition of a phenylenediamine compound to ameliorate soot-induced kinematic viscosity increase of lubricating oil compositions for diesel engines, particularly heavy duty diesel engines equipped with EGR systems. Also, it lists the following further references relating to phenylenediamines: U.S. Pat. No. 5,207,939, U.S. Pat. No. 5,213,699; and U.S. Pat. No. 5,298,662.

Phenylenediamines were known to act effectively as antioxidants; however they were found to be disadvantageous commercially because their presence, when used in amounts conventionally used to provide antioxidancy, displayed adverse effects on piston deposit and varnish control, and also displayed aggressiveness toward fluoroelastomeric engine seal materials. These adverse effects are particularly apparent with phenylenediamine compounds having higher nitrogen contents (compounds having relatively small hydrocarbyl substituents).

A problem in the prior art is to provide phenylenediamines that meet the above disadvantages and also to provide phenylenediamines that mitigate oxidative degradation in greases, fuels and functional fluids.

SUMMARY OF THE INVENTION

The invention ameliorates the above problem by providing phenylenediamines derived from Michael adducts that do not have higher nitrogen contents.

Thus, in a first aspect, the invention provides a composition in the form of a lubricating oil composition, grease, fuel, or functional fluid subject to oxidative degradation, containing, in the form of a Michael adduct, a phenylenediamine additive of the general formula (I).

$$R^1R^2N-Ar-NR^3CHR^4CHR^5COR^6 \qquad (I)$$

where $R^1$, $R^2$ and $R^3$ are independently hydrogen atoms, linear or branched alkyl or alkoxyalkyl groups, cycloalkyl rings, aryl groups or structure (II) below;

Ar is an aryl group;

$R^4$ and $R^5$ are independently hydrogen atoms, or alkyl, alkoxyalkyl or aryl groups;

$R^6$ is an alkyl, alkoxyalkyl, or alkylthioalkyl group, optionally connected to the carbon atom of the carbonyl group in the above general formula (I) via an oxygen atom;

structure (II) is represented by the formula $$-CHR^7CHR^8COR^9 \qquad (II)$$

where $R^7$ and $R^8$ are independently hydrogen atoms, or alkyl, alkoxyalkyl or aryl groups; and $R^9$ is an alkyl, alkoxyalkyl or alkylthioalkyl group and is optionally connected to the carbon atom of the carbonyl group in structure (II) via an oxygen atom;

the alkyl groups referred to above having from 1 to 36 carbon atoms, and the phenylenediamine being in the form of a free base or an oil-soluble salt thereof.

In a second aspect, the invention provides a method of reducing deposit formation and/or reducing metal corrosion in an internal combustion engine comprising operating the engine and lubricating the crankcase of the engine with a lubricating oil composition according to the first aspect of the invention.

In a third aspect, the invention provides the use of an oil-soluble or oil-dispersible phenylenediamine as defined in the first aspect of the invention to reduce, in the lubrication of an internal combustion engine, deposit formation and/or metal corrosion.

In this specification, the following words and expressions, if used, have the meanings ascribed below:

"active ingredients" or "(a.i.)" refers to additive material that is not diluent or solvent, and all weight or mass percentages expressed herein are based on a.i. context of the additive, and for upon the total weight of any additive package;

"comprising" or any cognate word specifies the presence of stated features, steps, or integers or components, but does not preclude the presence or addition of one or more other features, steps, integers, components or groups thereof. The expressions "consists of" or "consists essentially of" or cognates may be embraced within "comprises" or cognates, wherein "consists essentially of" permits inclusion of substances not materially affecting the characteristics of the composition to which it applies;

"hydrocarbyl" means a chemical group of a compound that contains hydrogen and carbon atoms and is bonded to the remainder of the compound directly via a carbon atom. The group may contain one or more atoms other than carbon and hydrogen ("hetero atoms") provided they do not affect the essentially hydrocarbyl mature of the group;

"major amount" means in excess of 50 mass % of a composition;

"minor amount" means less than 50 mass % of a composition.

Also, it will be understood that various components used, essential as well as optimal and customary, may react under conditions of formulation, storage or use and that the invention also provides the product obtainable or obtained as a result of any such reaction.

Further, it is to be understood that any upper and lower quantity, range and ratio limits set forth herein may be independently combined.

DETAILED DESCRIPTION OF THE INVENTION

The features of the invention relating, where appropriate, to each and all aspects of the invention, will now be described in more detail as follows:

Phenylenediamines

Significant deposit-control in lubricating oil compositions may be found not only for para-substituted phenylenediamines but for ortho- and meta-substituted phenylenediamines as well. Phenylenediamines with substitution on the centre aromatic ring Ar may also be highly-active deposit control agents.

In the phenylenediamines of the invention, preferably $R^6$ and $R^9$ independently contain from 6 to 24 carbon atoms. Further, when any of $R^1$, $R^2$, $R^3$, $R^4$, $R^5$, $R^7$ and $R^8$ is an alkyl or alkoxyalkyl group, it or they preferably contain 1 to 22, more preferably 1 to 12, carbon atoms.

Preferably, Ar is a substituted phenyl group and at least one of $R^1$, $R^2$, and $R^3$ is a hydrogen atom; or $R^1$ is a phenyl group, $R^2$ is a hydrogen atom and Ar is a phenyl group.

More preferably, $R^6$ is an alkylthioalkyl group containing 6 to 24, such as 8 to 12, carbon atoms that is bonded to the carbonyl group in the general formula (I) via an oxygen atom; and $R^3$ is a hydrogen atom, alkyl or alkoxyalkyl group or has structure (II), where $R^9$ is an alkyl, alkoxyalkyl or alkylthioalkyl group containing 6 to 24, such as 8 to 12, carbon atoms and is bonded to the carbon atom of the carbonyl group of general formula (I) via an oxygen atom.

When cycloalkyl groups are present, there may be one, two, three or four such groups in the Michael adduct molecule. Such cycloalkyl groups preferably contain 5, 6, 7 or 8 carbon atoms.

The phenylenediamines of the invention are made by the Michael addition reaction. Subject to their particular structure, they may be made directly by the Michael addition reaction, or they may be made from a Michael adduct intermediate such as by transesterifying a Michael adduct.

For example, in a first embodiment, they may be made by reacting, in a Michael addition, a phenylenediamine compound with an acrylate derived from an alkanol containing from 6 to 24 carbon atoms in the presence of a catalyst at a temperature in the range of 0 to 200° C.

In a second embodiment, they may be made by (i) reacting, in a Michael addition, a phenylenediamine compound with an acrylate derived from an alkanol containing from 1 to 4 carbon atoms in the presence of a catalyst at a temperature in the range of 0 to 200° C. to give an intermediate, and (ii) transesterifying the intermediate with an alkanol containing from 6 to 24 carbon atoms in the presence of an acid or metal catalyst and in an organic solvent at a temperature in the range of 0 to 200° C.

In the Michael addition reactions of the above embodiments, the catalyst may for example be acetic acid or phosphoric acid or an amberlyst catalyst. In step (ii) of the second embodiment above, the catalyst may for example be a clay catalyst or a titanium catalyst or an aluminum catalyst.

Preferably, the phenylenediamine has, or have on average, a nitrogen content of from 4 to 14, preferably from 5 to 11, more preferably from 5.5 to 10.5, mass %.

Lubricating Oil Compositions

Lubricating oil compositions useful in the practice of the present invention comprise a major amount of oil of lubricating viscosity and a minor amount of at least one of the phenylenediamine compounds.

Oils of lubricating viscosity useful in the context of the present invention may be selected from natural lubricating oils, synthetic lubricating oils and mixtures thereof. The lubricating oil may range in viscosity from light distillate mineral oils to heavy lubricating oils such as gasoline engine oils, mineral lubricating oils and heavy duty diesel oils. Generally, the viscosity of the oil ranges from 2 to 40, especially from 4 to 20, centistokes, as measured at 100° C.

Natural oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Oils of lubricating viscosity derived from coal or shale also serve as useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs and homologs thereof. Also useful are synthetic oils derived from a gas to liquid process from Fischer-Tropsch synthesized hydrocarbons, which are commonly referred to as gas to liquid, or "GTL," base oils.

Alkylene oxide polymers and interpolymers and derivatives thereof where the terminal hydroxyl groups have been modified by esterification or etherification constitute another class of known synthetic lubricating oils. These are exemplified by polyoxyalkylene polymers prepared by polymerization of ethylene oxide or propylene oxide, and alkyl and aryl ethers of polyoxyalkylene polymers (e.g., methyl-polyisopropylene glycol ether having a molecular weight of 1000 or diphenyl ether of poly-ethylene glycol having a molecular weight of 1000 to 1500); and mono- and polycarboxylic esters thereof, for example, acetic acid esters, mixed $C_3$-$C_8$ fatty acid esters and $C_{13}$ oxo acid diester of tetraethylene glycol.

Another suitable class of synthetic lubricating oils comprises esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dicicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl) silicate, tetra-(4-methyl-2-ethylhexyl)silicate, tetra-(p-tert-butyl-phenyl) silicate, hexa-(4-methyl-2-ethylhexyl)disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

The oil of lubricating viscosity may comprise a Group I, Group II, or Group III base stock or base oil blends of the aforementioned base stocks. Preferably, the oil of lubricating viscosity is a Group II or Group III base stock, or a mixture thereof, or a mixture of a Group I base stock and one or more of a Group II and Group III. Preferably, a major amount of the oil of lubricating viscosity is a Group II, Group III, Group IV or Group V base stock, or a mixture thereof. The base stock, or base stock blend preferably has a saturate content of at least 65, more preferably at least 75, such as at least 85, % by weight. Most preferably, the base stock, or base stock blend, has a saturate content of greater than 90%. Preferably, the oil or oil blend will have a sulfur content of less than 1, preferably less than 0.6, and most preferably less than 0.4, % by weight.

Preferably the volatility of the oil or oil blend, as measured by the Noack volatility test (ASTM D5880), is less than or equal to 30, preferably less than or equal to 25, more preferably less than or equal to 20, most preferably less than or equal 16, %. Preferably, the viscosity index (VI) of the oil or oil blend is at least 85, preferably at least 100, most preferably from about 105 to 140.

Definitions for the base stocks and base oils in this invention are the same as those found in the AMERICAN PETROLEUM INSTITUTE (API) PUBLICATION "Engine Oil Licensing and Certification System," Industry Services Department (14th Ed., December 1996), Addendum 1, December 1998. Said publication categorizes base stocks as follows:
(a) Group I base stocks contain less than 90 percent saturates and/or greater than 0.03 percent sulfur and have a viscosity index greater than or equal to 80 and less than 120 using the test methods specified in Table 1.
(b) Group II base stocks contain greater than or equal to 90 percent saturates and less than or equal to 0.03 percent sulfur and have a viscosity index greater than or equal to 80 and less than 120 using the test methods specified in Table 1.
(c) Group III base stocks contain greater than or equal to 90 percent saturates and less than or equal to 0.03 percent sulfur and have a viscosity index greater than or equal to 120 using the test methods specified in Table 1.
(d) Group IV base stocks are polyalphaolefins (PAO).
(e) Group V base stocks include all other base stocks not included in Groups I, II, III, or IV.

TABLE 1

Analytical Methods for Base Stock

| Property | Test Method |
|---|---|
| Saturates | ASTM D 2007 |
| Viscosity Index | ASTM D 2270 |
| Sulfur | ASTM D 2622 |
|  | ASTM D 4294 |
|  | ASTM D 4927 |
|  | ASTM D 3120 |

Co-Additives

Additional additives may be incorporated in the compositions of the invention to enable them to meet particular requirements. Examples of additives which may be included in lubricating oil compositions are dispersants, detergents, metal rust inhibitors, viscosity index improvers, corrosion inhibitors, oxidation inhibitors, friction modifiers, other dispersants, anti-foaming agents, anti-wear agents and pour point depressants. Some are discussed in further detail below.

Lubricating oil compositions of the present invention may further contain one or more ashless dispersants, which effectively reduce formation of deposits upon use in gasoline and diesel engines, when added to lubricating oils. Ashless dispersants useful in the compositions of the present invention comprises an oil-soluble polymeric long chain backbone having functional groups capable of associating with particles to be dispersed. Typically, such dispersants comprise amine, alcohol, amide or ester polar moieties attached to the polymer backbone, often via a bridging group. The ashless dispersant may be, for example, selected from oil-soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

Preferred dispersants include polyamine-derivatized poly alpha-olefin dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using 0.3 to 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trismethylolaminomethane, as described in U.S. Pat. No. 3,632,511.

Another class of ashless dispersants comprises Mannich base condensation products. Generally, these products are prepared by condensing one mole of an alkyl-substituted mono- or polyhydroxy benzene with 1 to 2.5 moles of carbonyl compound(s) (e.g., formaldehyde and paraformaldehyde) and 0.5 to 2 moles of polyalkylene polyamine, as disclosed, for example, in U.S. Pat. No. 3,442,808. Such Mannich base condensation products may include a polymer product of a metallocene-catalyzed polymerization as a substituent on the benzene group, or may be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified above.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide, boron acids and esters of boron acids, in an amount sufficient to provide from 0.1 to 20 atomic proportions of boron for each mole of acylated nitrogen composition. Useful dispersants contain from 0.05 to 2.0, e.g., from 0.05 to 0.7, mass % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from 0.5 to 4, e.g., from 1 to 3, mass % (based on the mass of acyl nitrogen compound) of a boron compound, preferably boric acid, usually as a slurry, to the acyl nitrogen compound and heating with stirring at from 135 to 190, e.g., 140 to 170, ° C., for from one to five hours, followed by nitrogen stripping. Alternatively, the boron treatment can be conducted by adding boric acid to a hot reaction mixture of the dicarboxylic acid material and amine, while removing water. Other post reaction processes commonly known in the art can also be applied.

The dispersant may also be further post treated by reaction with a so-called "capping agent." Conventionally, nitrogen-containing dispersants have been "capped" to reduce the adverse effect such dispersants have on the fluoroelastomer engine seals. Numerous capping agents and methods are known. Of the known "capping agents," those that convert basic dispersant amino groups to non-basic moieties (e.g., amido or imido groups) are most suitable. The reaction of a nitrogen-containing dispersant and alkyl acetoacetate (e.g., ethyl acetoacetate (EAA)) is described, for example, in U.S. Pat. Nos. 4,839,071, 4,839,072, and 4,579,675. The reaction of a nitrogen-containing dispersant and formic acid is described, for example, in U.S. Pat. No. 3,185,704. The reaction product of a nitrogen-containing dispersant and other suitable capping agents are described in U.S. Pat. No. 4,663,064 (glycolic acid); U.S. Pat. Nos. 4,612,132, 5,334,321, 5,356,552, 5,716,912, 5,849,676, and 5,861,363 (alkyl and alkylene carbonates, e.g., ethylene carbonate); U.S. Pat. No. 5,328,622 (mono-epoxide); U.S. Pat. No. 5,026,495; U.S. Pat. Nos. 5,085,788, 5,259,906, 5,407,591 (poly (e.g., bis)-epoxides); and U.S. Pat. No. 4,686,054 (maleic anhydride or succinic anhydride). The foregoing list is not exhaustive and other methods of capping nitrogen-containing dispersants are known to those skilled in the art.

For adequate piston deposit control, a nitrogen-containing dispersant can be added in an amount providing the lubricating oil composition with from 0.03 to 0.15, preferably from 0.07 to 0.12, mass % of nitrogen.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more.

Detergents that may be used include oil-soluble neutral and overbased sulfonates, phenates, sulfurized phenates, thiophosphonates, salicylates, naphthenates, and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl-substituted aromatic hydrocarbons such as those obtained from the fractionation of petroleum or by the alkylation of aromatic hydrocarbons. Examples included those obtained by alkylating benzene, toluene, xylene, naphthalene, diphenyl, or their halogen derivatives such as chlorobenzene, chlorotoluene and chloronaphthalene. The alkylation may be carried out in the presence of a catalyst with alkylating agents having from 3 to more than 70 carbon atoms. The alkaryl sulfonates usually contain from 9 to 80 or more, preferably from 16 to 60, carbon atoms per alkyl-substituted aromatic moiety.

The oil-soluble sulfonates or alkaryl sulfonic acids may be neutralized with oxides, hydroxides, alkoxides, carbonates, carboxylate, sulfides, hydrosulfides, nitrates, borates, and ethers of the metal. The amount of metal compound is chosen having regard to the desired TBN of the final product but typically ranges from 100 to 220, preferably at least 125, mass % of that stoichiometrically required.

Metal salts of phenols and sulfurized phenols are prepared by reaction with an appropriate metal compound such as an oxide or hydroxide, and neutral or overbased products may be obtained by methods known in the art. Sulfurized phenols may be prepared by reacting a phenol with sulfur or a sulfur-containing compound such as hydrogen sulfide, sulfur monohalide, or sulfur dihalide, to form products which are generally mixtures of compounds in which two or more phenols are bridged by sulfur-containing bridges.

Dihydrocarbyl dithiophosphate metal salts are frequently used as antiwear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2, wt. %, based upon the total weight of the lubricating oil composition. They may be prepared in accordance with known techniques by first forming a dihydrocarbyl dithiophosphoric acid (DDPA), usually by reaction of one or more alcohols or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides, and carbonates are most generally employed. Commercial additives frequently contain an excess of zinc due to the use of an excess of the basic zinc compound in the neutralization reaction.

The preferred zinc dihydrocarbyl dithiophosphates are oil-soluble salts of dihydrocarbyl dithiophosphoric acids and may be represented by the formula:

[RO(R'O)PSS]$_2$Zn wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups containing 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be five or greater. The zinc dihydrocarbyl dithiophosphate can therefore comprise zinc dialkyl dithiophosphates. The present invention may be particularly useful when used with passenger car diesel engine lubricant compositions containing phosphorus levels of from 0.02 to 0.12, such as from 0.03 to 0.10, or from 0.05 to 0.08, mass %, based on the total mass of the composition, and heavy duty diesel engine lubricant compositions containing phosphorus levels of from 0.02 to 0.16, such as from 0.05 to 0.14, or from 0.08 to 0.12, mass %, based on the total mass of the composition. In one preferred embodiment, lubricating oil compositions of the present invention contain zinc dialkyl dithiophosphate derived predominantly (e.g., over 50, such as over 60, mol. %) from secondary alcohols.

Oxidation inhibitors or antioxidants reduce the tendency of mineral oils to deteriorate in service. Oxidative deterioration can be evidenced by sludge in the lubricant, varnish-like deposits on the metal surfaces and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorus esters, metal thiocarbamates, oil soluble copper compounds as described in U.S. Pat. No. 4,867,890, and molybdenum-containing compounds.

Typical oil-soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —SO$_2$— or alkylene group) and two are directly attached to one amine nitrogen are also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups.

Multiple antioxidants are commonly employed in combination. In one preferred embodiment, lubricating oil compositions of the present invention, in addition to the phenylenediamine compound(s) added to ameliorate soot-induced viscosity increase, contain from 0.1 to 1.2 mass % of aminic antioxidant and from 0.1 to 3 mass % of phenolic antioxidant. In another preferred embodiment, lubricating oil compositions of the present invention contain from 0.1 to 1.2 mass % of aminic antioxidant, from 0.1 to 3 mass % of phenolic antioxidant and a molybdenum compound in an amount providing the lubricating oil composition with from 10 to 1000 ppm by weight of molybdenum. Preferably, lubricating oil compositions useful in the practice of the present invention, particularly lubricating oil compositions useful in the practice of the present invention that are required to contain no greater than 1200 ppm of phosphorus, contain ashless antioxidants other than phenylenediamines, in an amount of from 0.1 to 5, preferably from 0.3 to 4, more preferably from 0.5 to 3, mass %. Where the phosphorus content is required to be lower, the amount of ashless antioxidant other than phenylenediamine will preferably be increased accordingly.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

A viscosity index improver dispersant functions both as a viscosity index improver and as a dispersant. Examples of viscosity index improver dispersants include reaction products of amines, for example, polyamines, with a hydrocarbyl-substituted mono- or dicarboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralised with an amine, hydroxyamine or an alcohol; or a polymer of ethylene with a $C_3$ to $C_{20}$ olefin further reacted either by grafting a $C_4$ to $C_{20}$ unsaturated nitrogen-containing monomer thereon or by grafting an saturated acid onto the polymer backbone and then reacting carboxylic acid groups of the grafted acid with an amine, hydroxy amine, or alcohol.

Friction modifiers and fuel economy agents that are compatible with the other ingredients of the final oil may also be included. Examples of such materials include glyceryl monoesters of higher fatty acids, for example, glyceryl monooleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil-soluble organo-molybdenum compounds include dithiocarbamates, dithiophosphates, dithiophosphinates, xanthates, thioxanthates and sulfides, and mixtures thereof. Particularly preferred are molybdenum dithiocarbamates, dialkyldithiophosphates, alkyl xanthates, and alkylthioxanthates.

Additionally, the molybdenum compound may be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkaline metal molybdates and other molybdenum salts, e.g., hydrogen sodium molybdate, MoOCl$_4$, MoO$_2$Br$_2$, Mo$_2$O$_3$Cl$_6$, molybdenum trioxide or similar acidic molybdenum compounds.

Among the molybdenum compounds useful in the compositions of this invention are organo-molybdenum compounds of the formula: $Mo(ROCS_2)_4$ and $Mo(RSCS_2)_4$ wherein R is an organo group selected from the group consisting of alkyl, aryl, aralkyl and alkoxyalkyl, generally of from 1 to 30, preferably 2 to 12, carbon atoms and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $Mo_3S_kL_nQ_z$ and mixtures thereof wherein L are independently selected ligands having organo groups with a sufficient number of carbon atoms to render the compound soluble or dispersible in the oil, n is from 1 to 4, k varies from 4 through 7, Q is selected from the group of neutral electron-donating compounds such as water, amines, alcohols, phosphines, and ethers, and z ranges from 0 to 5 and includes non-stoichiometric values. At least 21 total carbon atoms should be present among all the ligand organo groups, such as at least 25, at least 30, or at least 35, carbon atoms.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane. Some of the above-mentioned additives can provide a multiplicity of effects; thus for example, a single additive may act as a dispersant-oxidation inhibitor. This approach is known.

In the present invention, it may be necessary to include an additive which maintains the stability of the viscosity of the blend. Thus, although polar group-containing additives achieve a suitably low viscosity in the pre-blending stage, it has been observed that some compositions increase in viscosity when stored for prolonged periods. Additives which are effective in controlling this viscosity increase include long chain hydrocarbons functionalized by reaction with mono- or dicarboxylic acids or anhydrides which are used in the preparation of the ashless dispersants as hereinbefore described.

When lubricating compositions contain one or more of the above-mentioned additives, each additive is typically blended into the base oil in an amount that enables the additive to provide its desired function. Representative effect amounts of such additives, when used in crankcase lubricants, are listed below. All the values listed are stated as mass percent active ingredient.

TABLE 2

| ADDITIVE | MASS % (Broad) | MASS % (Preferred) |
|---|---|---|
| Metal Detergents | 0.1-15 | 0.2-9 |
| Corrosion Inhibitor | 0-5 | 0-1.5 |
| Metal Dihydrocarbyl Dithiophosphate | 0.1-6 | 0.1-4 |
| Antioxidant | 0-5 | 0.01-3 |
| Pour Point Depressant | 0.01-5 | 0.01-1.5 |
| Antifoaming Agent | 0-5 | 0.001-0.15 |
| Supplemental Antiwear Agents | 0-1.0 | 0-0.5 |
| Friction Modifier | 0-5 | 0-1.5 |
| Viscosity Modifier | 0.01-10 | 0.25-3 |
| Basestock | Balance | Balance |

Fully Formulated Oils

Fully formulated passenger car diesel engine lubricating oil (PCDO) compositions of the present invention preferably have a sulfur content of less than 0.4, such as less than 0.35, more preferably less than 0.03, such as less than 0.15, mass %. Preferably, the Noack volatility of the fully formulated PCDO (oil of lubricating viscosity plus all additives) will be no greater than 13, such as no greater than 12, preferably no greater than 10. Fully formulated PCDOs of the present invention preferably have no greater than 1200, such as no greater than 1000, or no greater than 800, ppm of phosphorus. Fully formulated PCDOs of the present invention preferably have a sulfated ash (SASH) content of 1.0 mass % or less.

Fully formulated heavy duty diesel engine (HDD) lubricating oil compositions of the present invention preferably have a sulfur content of less than 1.0, such as less than 0.6, more preferably less than 0.4, such as less than 0.15, mass %. Preferably, the Noack volatility of the fully formulated HDD lubricating oil composition (oil of lubricating viscosity plus all additives) will be no greater than 20, such as no greater than 15, preferably no greater than 12. Fully formulated HDD lubricating oil compositions of the present invention preferably have no greater than 1600, such as no greater than 1400, or no greater than 1200, ppm of phosphorus. Fully formulated HDD lubricating oil compositions of the present invention preferably have a sulfated ash (SASH) content of 1.0 mass % or less.

Concentrates

It may be desirable, although not essential, to prepare one or more additive concentrates comprising additives (concentrates sometimes being referred to as additive packages) whereby several additives can be added simultaneously to the oil to form the lubricating oil composition. A concentrate for the preparation of a lubricating oil composition of the present invention may, for example, contain from 0.1 to 16 mass % of phenylenediamine; 10 to 40 mass % of a nitrogen-containing dispersant; 2 to 20 mass % of an aminic antioxidant and/or a phenolic antioxidant, a molybdenum compound, or a mixture thereof; 5 to 40 mass % of a detergent; and from 2 to 20 mass % of a metal dihydrocarbyl dithiophosphate.

The final composition may employ from 5 to 25, preferably 5 to 18, typically 10 to 15, mass % of the concentrate, the remainder being oil of lubricating viscosity and viscosity modifier.

Fuels

As mentioned above, the substituted phenylenediamines may be used as additives in fuels. As examples of fuels, the following may be monitored.

Oil Derived from Plant or Animal Material

Oils and fats derived from plant or animal materials are increasingly finding application as fuels and in particular, as partial or complete replacements for petroleum derived middle distillate fuels such as diesel. Commonly, such fuels are known as 'biofuels' or 'biodiesel'. Biofuels may be derived from many sources. Amongst the most common are the alkyl, often methyl, esters of fatty acids extracted from plants such as rapeseed and sunflower. These types of fuel are often referred to as FAME (fatty acid methyl esters).

Examples of oils and fats derived from animal or vegetable material are rapeseed oil, coriander oil, soyabean oil, cottonseed oil, sunflower oil, castor oil, olive oil, peanut oil, maize oil, almond oil, palm kernel oil, coconut oil, mustard seed oil, jatropha oil, beef tallow and fish oils. Further examples include oils derived from corn, jute, sesame shea nut, ground nut and linseed oil and may be derived there from by methods known in the art. Rapeseed oil, which is a mixture of fatty acids partially esterified with glycerol, is available in large quantities and can be obtained in a simple way by pressing from rapeseed. Recycled oils such as used kitchen oils are also suitable.

As alkyl esters of fatty acids, consideration may be given to the following, for example as commercial mixtures: the ethyl, propyl, butyl and especially methyl esters of fatty acids with 12 to 22 carbon atoms, for example of lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Mixtures with particularly advantageous properties are those which contain mainly, i.e. to at least 50 wt % methyl esters of fatty acids with 16 to 22 carbon atoms and 1, 2 or 3 double bonds. The preferred lower alkyl esters of fatty acids are the methyl esters of oleic acid, linoleic acid, linolenic acid and erucic acid.

Commercial mixtures of the stated kind are obtained for example by cleavage and esterification of animal and vegetable fats and oils by their transesterification with lower aliphatic alcohols. For production of alkyl esters of fatty acids it is advantageous to start from fats and oils which contain low levels of saturated acids, less than 20%, and which have an iodine number of less than 130. Blends of the following esters or oils are suitable, e.g. rapeseed, sunflower, coriander, castor, soyabean, peanut, cotton seed and beef tallow. Alkyl esters of fatty acids based on a new variety of rapeseed oil, the fatty acid component of which is derived to more than 80 wt % from unsaturated fatty acids with 18 carbon atoms, are preferred.

Particularly preferred are oils capable of being utilised as biofuels. Biofuels, i.e. fuels derived from animal or vegetable material, are believed to be less damaging to the environment on combustion, and are obtained from a renewable source. It has been reported that on combustion less carbon dioxide is formed than by the equivalent quantity of petroleum distillate fuel, e.g. diesel fuel, and very little sulphur dioxide is formed. Certain derivatives of vegetable oil, e.g. those obtained by saponification and re-esterification with a monohydric alkyl alcohol, may be used as a substitute for diesel fuel.

Thus, a biofuel is an oil obtained from vegetable or animal material, or both, or a derivative thereof, capable of being utilised as a fuel.

Whilst many of the above oils may be used as biofuels, preferred are vegetable oil derivatives, of which particularly preferred biofuels are alkyl ester derivatives of rapeseed oil, cottonseed oil, soyabean oil, sunflower oil, olive oil, or palm oil, rapeseed oil methyl ester being especially preferred, either alone or in admixture with other vegetable oil derivatives e.g. mixtures in any proportion of rapeseed oil methyl ester and palm oil methyl ester.

At present, biofuels are most commonly used in combination with petroleum-derived oils. The present invention is applicable to mixtures of biofuel and petroleum-derived fuels in any ratio. For example, at least 5, preferably at least 25, more preferably at least 50, for example at least 95, % by weight of the oil may be derived from a plant or animal source.

Diesel Fuel

Preferably, the diesel fuel is a petroleum-based fuel oil, especially a middle distillate fuel oil. Such distillate fuel oils generally boil within the range of from 110 to 500, e.g. 150 to 400, ° C. The fuel oil may comprise atmospheric distillate or vacuum distillate, cracked gas oil, or a blend in any proportion of straight run and thermally and/or refinery streams such as catalytically cracked and hydro-cracked distillates.

Other examples of diesel fuels include Fischer-Tropsch fuels. Fischer-Tropsch fuels, also known as FT fuels, include those described as gas-to-liquid (GTL) fuels, biomass-to-liquid (BTL) fuels and coal conversion fuels. To make such fuels, syngas ($CO+H_2$) is first generated and then converted to normal paraffins by a Fischer-Tropsch process. The normal paraffins may then be modified by processes such as catalytic cracking/reforming or isomerisation, hydrocracking and hydroisomerisation to yield a variety of hydrocarbons such as iso-paraffins, cyclo-paraffins and aromatic compounds. The resulting FT fuel can be used as such or in combination with other fuel components and fuel types. Also suitable are diesel fuels derived from plant or animal sources such as FAME. These may be used alone or in combination with other types of fuel.

Preferably, the diesel fuel has a sulphur content of at most 0.05%, more preferably of at most 0.035%, especially of at most 0.015, % by weight. Fuels with even lower levels of sulphur are also suitable such as, fuels with less than 50, preferably less than 20, for example 10 ppm sulphur by weight or less.

Functional Fluids

As indicated above, the compositions of invention may find application as functional fluids. These are fluids that provide a medium through which power is transferred in order to drive, control and/or move. They are fluids designed for hydrodynamic applications known as power-transmission oils and fluids for hydrostatic applications known as hydraulic oils. The fluid is treated like a machine element in the planning, realisation and commissioning of systems including such a fluid, and consists of a base fluid (base oil) and additives, the types of which determine the properties and classification of the functional fluid.

Grease

As mentioned above, the substituted phenylenediamines may be used as additives in greases. Greases are often used in place of oils for lubrication where the lubricant is required to maintain its position in a mechanism and where opportunities for frequent re-lubrication may be limited or not economically justified. Examples include the use of grease on bearings, axles, hinges, gears, and sliding parts.

Greases are composed of a lubricating fluid, such as a mineral oil or synthetic oil, or combination thereof, and a thickener, such as a metal soap. Additional small quantities of other conventional additives may also be included in the grease formulation, those other additional additives being, for example, extreme pressure agents, antioxidants, dyes, other rust and/or corrosion inhibitors, tackiness agents, oiliness agents, and viscosity index improvers.

The lubricating base oil that is used in preparing the grease compositions can be any of the conventionally-used mineral oils, synthetic hydrocarbon oils or synthetic ester oils. Mineral lubricating oil base stocks used in preparing the greases can be any conventionally refined base stocks derived from a paraffinic, naphthenic and mixed base crudes. Conventional refinery techniques include, for example, distillation, solvent or catalytic dewaxing, solvent extraction, hydrofinishing, hydrocracking, and vis-breaking.

Synthetic oils that can be used include synthetic hydrocarbons such as polyolefins including polybutene, polyisobutenes and especially the polyalphaolefins (PAO). Such poly-alphaolefins may be produced from linear alpha olefins usually containing about 8-12 carbon atoms by an oligomerization process which produces dimers, trimers, tetramers, pentamers, etc. of these olefins. The resulting oligomer is usually hydrogenated to produce a saturated hydrocarbon. The most widely used polyalphaolefins are poly-1-decenes.

Other suitable synthetic hydrocarbon oils include alkyl benzenes (e.g. alkylate bottoms from the alkylation of benzene with tetrapropylene), the copolymers of ethylene and propylene, or the high VI isoparaffins produced by hydrocracking or hydroisomerization of waxes.

Included in the group of synthetic oils are those recovered from tar sands, shale oil, light hydrocarbons produced via, for example, the Fisher-Tropsch process for converting synthesis gas (CO and hydrogen) into hydrocarbons, wax isomerate oils produced by the catalytic hydroisomerization of natural petroleum waxes (i.e., slack wax) or synthetic waxes (i.e., Fischer-Tropsch waxes) or mixtures of such waxes.

Other synthetic lubricating oils that can be used include silicone oils (e.g. ethyl phenyl polysiloxanes, and methyl polysiloxanes), polyglycol oils, (e.g., those obtained by condensing butyl alcohol with propylene oxide), and carbonate esters (e.g., the product of reacting $C_8$ oxo alcohol with ethyl carbonate to form a half ester followed by reaction of the latter with tetraethylene glycol for example). Still further synthetic lubricating oils that can be used include polyphenyl ethers; esters of dibasic acids such as di-2-ethylhexyl sebacate, esters of poly glycols such as trimethylol propane tricaprylate, pentaerythritol tetraoctanoate; dipentaerythritol tricaprylate tripelargonate esters of glycols such as $C_{13}$ oxo acid diester of tetraethylene glycol, or complex esters such as one formed from 1 mole of sebacic acid and 2 moles of tetraethylene glycol and 2 moles of 2-ethylhexanoic acid.

A variety of thickening agents for greases have been developed including the alkali and alkaline earth metal and aluminum soaps; and particularly those of sodium, lithium, calcium, barium and aluminum. Other thickeners include clays and modified clays, polyureas, asbestos, carbon black, silica gels, aluminum complexes, polymers, phthalocyanine, and indanthrene. A suitable soap may be a salt of an alkali metal such as lithium, sodium or potassium or an alkaline earth metal such as calcium, strontium, barium or magnesium. Commonly used fatty acids include stearic acid, hexanoic acid, oleic acid, azelaic acid, and 12-hydroxystearic acid. The most widely-used thickener for greases is lithium 12-hydroxystearate.

EXAMPLES

The invention will now be particularly described in the following examples which are not intended to limit the scope of the claims hereof.
Preparation of Phenylenediamines

Example 1

Preparation of
3-(4-phenylamino-phenylamino)-propanoic acid
methyl ester: Michael Addition of
4-aminodiphenylamine with methyl acrylate N-phenyl-p-phenylenediamine (4-ADPA; 162 g) and methyl acrylate (120 ml) were charged into a 4-neck 500 mL round-bottom flask equipped with mechanical stirrer, condenser/Dean-Start trap, and inlets for nitrogen. It was heated to 80° C. to dissolve all the 4-ADPA. Acetic acid (24.8 ml) was add followed by reflux for 2-3 h. The mixture was cooled to room temperature, treated with ethyl acetate (400 mL), washed with 10% NaOH solution (400 mL), water, brine, and dried ($Na_2SO_4$). The solvent was rotary evaporated to obtain about 233 g of product. The completion of reaction was confirmed by FT-IR and HPLC. The structure of the product was confirmed by 1H and 13C-NMR.

Example 2

Preparation of 3-(4-phenylamino-phenylamino)-propanoic acid 2-(octylthio)ethyl ester: Transesterification of 3-(4-phenylamino-phenylamino)-propanoic acid methyl ester with 2-hydroxyethyl n-octylsulfide 3-(4-Phenylamino-phenylamino)-propanoic acid methyl ester (30 g), 2-hydroxyethyl n-octylsulfide (29 ml) and toluene (100 ml) were placed in a 4-neck 500 mL round-bottom flask equipped with a stirrer, Dean & Stark receiver, condenser, thermocouple and nitrogen inlet. The reaction was then heated under reflux at 110-115° C. under a stream of nitrogen, and toluene (30 mL) entrained in the Dean & Start side arm was removed. Titanium isopropoxide (3.3 mL) was added into the reaction under a stream of nitrogen. The reaction was refluxed for 24 h until the completion of reaction as determined by HPLC. The cooled toluene solution was then washed with 10% HCl solution, 5% NaOH solution, water, brine, and dried ($Na_2SO_4$). The solvent was rotary evaporated to obtain about 21 g of crude material, which was subjected to Kugelrohr distillation to give 14.8 g of product. The structure of the product was confirmed by 1H and 13C-NMR.

Example 3

One-Step Preparation of
3-(4-Phenylamino-phenylamino)-propanoic acid
isodecyl ester: Michael Addition of
4-aminodiphenylamine with isodecyl acrylate N-phenyl-p-phenylenediamine (4-ADPA; 40 g) and isodecyl acrylate (53 ml) were charged into a 4-neck 250 mL round-bottom flask equipped with a mechanical stirrer, a condenser/Dean-Stark trap, and inlets for nitrogen. It was heated to 80° C. to dissolve all the 4-ADPA. Acetic acid (6 ml) was added followed by reflux for 5 h. The mixture was cooled to room temperature, treated with ethyl acetate (400 ml) washed with 10% hydrochloric acid, 10% NaOH solution, water, brine, and dried ($Na_2SO_4$). The solvent was rotary evaporated to obtain about 76 g of product. The completion of reaction was confirmed by FT-IR and HPLC. The structure of the product was confirmed by 1H and 13C-NMR.

Example 4

Preparation of
3-(4-phenylamino-phenylamino)-dipropanoic acid
dimethyl ester: Michael Addition of
4-aminodiphenylamine with 2 equivalent methyl
acrylate N-phenyl-p-phenylenediamine (4-ADPA; 100 g) and methyl acrylate (146.6 ml) were charged into a 4-neck 500 mL round-bottom flask equipped with a mechanical stirrer, a condenser/Dean-Stark trap, and inlets for nitrogen. It was heated to 80° C. to dissolve all the 4-ADPA. Acetic acid (15.5 ml) was added followed by reflux for 24 h. The mixture was cooled to room temperature, treated with ethyl acetate (400 mL), and washed with 10% NaOH solution (400 mL), water, brine, and dried ($Na_2SO_4$). The solvent was rotary evaporated to obtain about 182 g of product. The completion of reaction was confirmed by FT-IR and HPLC. The structure of the product was confirmed by 1H and 13C-NMR.

Example 5

Preparation of 3-(4-phenylamino-phenylamino)-dipropanoic acid di(2-(octylthio)ethyl) ester: transesterification of 3-(4-phenylamino)-dipropanoic acid dimethyl ester with 2-hydroxyethyl n-octylsulfide 3-(4-Phenylamino-phenylamino)-dipropanoic acid dimethyl ester (20 g), 2-hydroxyethyl n-octylsulfide (34.5 ml) and toluene (200 ml) were placed in a 4-neck 500 mL round-bottom flask equipped with a stirrer, Dean & Stark receiver, condenser, thermocouple and nitrogen inlet. The reaction was then heated under reflux at 100-115° C. under a stream of nitrogen, toluene (30 mL) entrained in the Dean & Stark side arm being removed. Titanium isopropoxide (3.3 mL) was added into the reaction under a stream of nitrogen. The reaction was refluxed for 48 h until the completion of reaction by HPLC. The cooled toluene solution was then washed with 10% HCl solution, 5% NaOH solution, water, brine, and dried ($Na_2SO_4$). The solvent was rotary evaporated to obtain about 32.4 g of crude material, which was subjected to Kugelrohr distillation to give 27 g of product. The structure of the product was confirmed by 1H and 13C-NMR.

Example 6

Preparation of N,N,N'-tricyclohexyl-N'-methoxypropionyl-para-phenylenediamine

A 100 ml 3-neck flask was fitted with an overhead stirrer, a thermocouple and a nitrogen inlet. The flask was charged with N,N,N'-tricyclohexyl-para-phenylenediamine (27.1 g), methyl acrylate (150 ml) and glacial acetic acid (10 ml). The reaction was stirred at 82° C. until complete. The reaction mass was taken up in xylenes, extracted with aqueous sodium hydroxide and washed three times with water. Solvent was removed by rotary evaporation. The reaction mass was taken up in hexanes. Some polymer precipitated and was removed. Solvent was removed by rotary evaporation. The product was taken up in xylenes and filtered. Solvent was removed by rotary evaporation. Remaining volatiles were removed by vacuum distillation (29", 196° C.) to yield a viscous, dark yellow liquid.

The completion of reaction was confirmed by FT-IR and HLPC. The structure of the product was confirmed by 1H and 13C-NMR.

Testing and Results
Antioxidant Activity

The products of Examples 2, 5 and 6 were each blended into fully-formulated crankcase lubricating compositions: one composition contained 0.44% by mass of the Example 5 product, and the other 0.29% by mass of the Example 2 product so as to be present on an equi-molar basis. The compositions were otherwise identical.

The compositions were evaluated against a base-line comparison in the form of a composition that lacked a phenylene diamine but that was otherwise identical. The evaluation took the form of the Mid-High Temperature Thermo-oxidation Engine Oil Simulation Test (MHT4-TEOST), part of the ILSAC GF-3 and GF-4, whose stated purpose is to measure the tendency of the oil to form deposits. It is however an anti-oxidancy test since deposits start to form when antioxidant becomes depleted.

The test determines the mass of a deposit formed on a specially constructed steel rod by continuously stressing a repetitive passage of 8.5 g of test oil under thermal-oxidative and catalytic conditions. The instrument used was manufactured by Tannas Co. and has a typical repeatability of 0.15(x+16) mg wherein x is the mean of two or more repeated test results. The TEOST test conditions are listed below. The lower the amount of deposits obtained, the better the oxidation stability of the oil.

| TEOST MHT Test Conditions | |
|---|---|
| Test Parameters | Settings |
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

The results, expressed as mg of deposits, are shown below:

| Phenylenediamine in Composition | Deposit |
|---|---|
| Example 2 | 23.1 |
| Example 3 | 33 |
| Example 5 | 32.4 |
| Example 6 | 38 |
| None (base-line comparison composition) | 46.7 |

The results demonstrate that both mono and di-substituted Michael addition products are highly effective in inhibiting deposit formation in the test in comparison with the base-line case.

Copper Corrosion Performance

The products of Examples 2 and 5 were each blended into fully-formulated heavy duty diesel engine lubricating oil compositions: one composition contained 0.44% by mass of the Example 5 product and the other 0.29 mass % of the Example 2 product so as to be present on an equi-molar basis. The compositions were otherwise identical. The compositions were evaluated against a base-line comparison in the form of a composition that lacked a phenylene diamine but that was otherwise identical.

The compositions were also evaluated against a reference composition in the form of an otherwise identical composition on an equi-molar basis that contained a phenylenediamine representative of those known in the art, namely an N-alkyl-N'-phenyl-para-phenylenediamine wherein the alkyl substituent was a secondary $C_{11}$ alkyl group ("sec $C_{11}$ PDA"). Thus, the phenylenediamines of the inventive composition and of the reference composition differed only in their substitution on one of the nitrogen atoms.

The evaluation took the form of the ASTM D6594-05 (HTCBT), which tests diesel engine lubricants to determine their tendency to corrode various metals such as copper alloys commonly used in cam followers and bearings.

The results, expressed as ppm by mass of copper, are shown below:

| Phenylenediamine in Composition | ppm |
|---|---|
| Example 2 | 7.6 |
| Example 5 | 6.2 |
| None (base-line comparison composition) | 5.4 |
| Sec $C_{11}$ PDA (reference comparison composition) | 172.6 |

The failing limit for the test is 20 ppm. Thus, the above results demonstrate acceptable performance of the Michael adduct-containing compositions (Exs 2 and 5) that is equivalent to the base-line comparison and that is much superior to the reference composition.

What is claimed is:

1. A composition in the form of a lubricating oil composition, grease, fuel, or functional fluid subject to oxidative degradation, containing, in the form of a Michael adduct, a phenylenediamine additive of the general formula (I)

$$R^1R^2N\text{—}Ar\text{—}NR^3CHR^4CHR^5COR^6 \qquad (I)$$

wherein:
R$^1$, R$^2$ and R$^3$ are independently hydrogen atoms, linear or branched alkyl or alkoxyakyl groups, cycloalkyl rings, or aryl groups, or structure (II) below;
Ar is an aryl group;
R$^4$ and R$^5$ are independently hydrogen atoms, or alkyl, alkoxyalkyl or aryl groups;
R$^6$ is an alkoxyalkyl group connected to the carbon atom of the carbonyl group in the above general formula (I) via an oxygen atom;
structure (II) is represented by the formula $$\text{—}CHR^7CHR^8COR^9 \qquad (II)$$

wherein R$^7$ and R$^8$ are independently hydrogen atoms, or alkyl, alkoxyalkyl or aryl groups; and
R$^9$ is an alkoxyalkyl group and is connected to the carbon atom of the carbonyl group in structure (II) via an oxygen atom;
the alkyl groups referred to above having from 1 to 36 carbon atoms, and the phenylenediamine being in the form of a free base or as an oil-soluble salt thereof.

2. A composition as claimed in claim 1, wherein R$^6$ and R$^9$ independently contain from 6 to 24 carbon atoms.

3. A composition as claimed in claim 1 wherein, when any of R$^1$, R$^2$, R$^3$, R$^4$, R$^5$, R$^7$ and R$^8$ is an alkyl or alkoxyalkyl group, it or they contain 1 to 22 carbon atoms.

4. A composition as claimed in claim 3 wherein, when any of R$^1$, R$^2$, R$^3$, R$^4$, R$^5$, R$^7$ and R$^8$ is an alkyl or alkoxyalkyl group, it or they contain 1 to 12 carbon atoms.

5. A composition as claimed in claim 2 wherein, when any of R$^1$, R$^2$, R$^3$, R$^4$, R$^5$, R$^7$ and R$^8$ is an alkyl or alkoxyalkyl group, it or they contain 1 to 22 carbon atoms.

6. A composition as claimed in claim 5, wherein, when any of R$^1$, R$^2$, R$^3$, R$^4$, R$^5$, R$^7$ and R$^8$ is an alkyl or alkoxyalkyl group, it or they contain 1 to 12 carbon atoms.

7. A composition as claimed in claim 1, wherein Ar is a substituted phenyl group and at least one of R$^1$, R$^2$ and R$^3$ is a hydrogen atom.

8. A composition as claimed in claim 2, wherein Ar is a substituted phenyl group and at least one of R$^1$, R$^2$ and R$^3$ is a hydrogen atom.

9. A composition as claimed in claim 3, wherein Ar is a substituted phenyl group and at least one of R$^1$, R$^2$ and R$^3$ is a hydrogen atom.

10. A composition as claimed in claim 7, wherein R$^1$ is a phenyl group, R$^2$ is a hydrogen atom and Ar is a phenyl group.

11. A composition as claimed in claim 8, wherein R$^1$ is a phenyl group, R$^2$ is a hydrogen atom and Ar is a phenyl group.

12. A composition as claimed in claim 9, wherein R$^1$ is a phenyl group, R$^2$ is a hydrogen atom and Ar is a phenyl group.

13. A composition as claimed in claim 10, wherein R$^6$ is an alkoxyalkyl group containing 6 to 24 carbon atoms that is bonded to the carbon atom of the carbonyl group in the formula (I) via an oxygen atom; and R$^3$ is a hydrogen atom, or alkyl or alkoxyalkyl group or has structure (II) where R$^9$ is an alkoxyalkyl group containing 6 to 24 carbon atoms and is bonded to the carbon atom of the carbonyl group in structure (I) via an oxygen atom.

14. A composition as claimed in claim 11, wherein R$^6$ is an alkoxyalkyl group containing 6 to 24 carbon atoms that is bonded to the carbon atom of the carbonyl group in the formula (I) via an oxygen atom; and R$^3$ is a hydrogen atom, or alkyl or alkoxyalkyl group or has structure (II) where R$^9$ is an alkoxyalkyl group containing 6 to 24 carbon atoms and is bonded to the carbon atom of the carbonyl group in structure (I) via an oxygen atom.

15. A composition as claimed in claim 12, wherein R$^6$ is an alkoxyalkyl group containing 6 to 24 carbon atoms that is bonded to the carbon atom of the carbonyl group in the formula (I) via an oxygen atom; and R$^3$ is a hydrogen atom, or alkyl or alkoxyalkyl group or has structure (II) where R$^9$ is an alkoxyalkyl group containing 6 to 24 carbon atoms and is bonded to the carbon atom of the carbonyl group in structure (I) via an oxygen atom.

16. The composition of claim 1 in the form of a lubricating oil composition comprising an oil of lubricating viscosity in a concentrate-forming amount.

17. The composition of claim to 1 in the form of a lubricating oil composition comprising an oil of lubricating viscosity in a major amount.

18. The composition of claim 16, further comprising one or more co-additives, different from the phenylenediamine, selected from ashless dispersants, metal detergents, corrosion inhibitors, metal dihydrocarbyl dithiophosphates, antioxidants, pour point depressants, friction modifiers, antifoam agents and viscosity modifiers.

19. The composition of claim 17, further comprising one or more co-additives, different from the phenylenediamine, selected from ashless dispersants, metal detergents, corrosion inhibitors, metal dihydrocarbyl dithiophosphates, antioxidants, pour point depressants, friction modifiers, antifoam agents and viscosity modifiers.

20. A method of reducing deposit formation and/or reducing metal corrosion in an internal combustion engine comprising operating the engine and lubricating the crankcase of the engine with a composition as claimed in claim 18.

* * * * *